United States Patent [19]

Woog et al.

[11] 4,088,759

[45] May 9, 1978

[54] INJECTABLE PHARMACEUTICAL SOLUTIONS

[75] Inventors: Heinrich Woog, Ludwigshafen am Rhein; Werner Gruber, Birkenau; Werner Rothe, Hockenheim, all of Germany

[73] Assignee: Boehringer Mannheim GmbH, Mannheim, Germany

[21] Appl. No.: 742,303

[22] Filed: Nov. 16, 1976

[30] Foreign Application Priority Data

Dec. 12, 1975 Germany ............................. 2556001

[51] Int. Cl.$^2$ .............................................. A61K 31/56
[52] U.S. Cl. .................................................... 424/240
[58] Field of Search ................................. 424/240, 241

[56] References Cited

U.S. PATENT DOCUMENTS

| 3,276,959 | 10/1966 | Ritter et al. | 424/240 |
| 3,487,152 | 12/1969 | Carstensen et al. | 424/240 |
| 3,963,834 | 6/1976 | Kuhn et al. | 424/240 |

*Primary Examiner*—Elbert L. Roberts
*Attorney, Agent, or Firm*—Burgess, Dinklage & Sprung

[57] ABSTRACT

Stable, physiologically compatible, injectable solutions comprising, as an active ingredient, an alkali metal salt of canrenoic acid or a mixture of an alkali metal canrenoate and a diuretic, and an aqueous, physiologically compatible alkaline buffer having a low buffer capacity and yielding a pH range of 10.2 to 11.2, e.g., tripotassium phosphate, potassium carbonate or potassium glycinate.

12 Claims, No Drawings

INJECTABLE PHARMACEUTICAL SOLUTIONS

The present invention is concerned with stable, physiologically compatible injection solutions ready for injection which contain as an active ingredient an alkali metal salt of canrenoic acid or a mixture of an alkali metal canrenoate and a diuretic.

Canrenoic acid, i.e., 3-(3-oxo-17beta-hydroxy-4,6-androstadien-17alpha-yl)-propionic acid, is a known compound, the water-soluble potassium salt of which is outstandingly useful in medicine as a diuretic. It can also be advantageously used in combination with other diuretics, for example, with 5-(4-chloro-5-sulfamoyl-2-thenylaminophenyl)-tetrazole, which is described in German Pat. No. 1,815,922 or with 4-chloro-N-(2-furylmethyl)-5-sulfamoyl-anthranilic acid (furosemide), which is described in German Pat. No. 1,122,541. It is also known to use the potassium salf of canrenoic acid alone in an injectable solution. Furthermore, it is known to administer, in two separate injections, potassium canrenoate and furosemide and to utilize the synergistic action of these agents. However, a stable solution of a combination has not been previously described.

An injectable combination preparation has been described in German Pat. No. 2,423,550; in this case, an injectable solution of a mixture of potassium canrenoate and 5-(4-chloro-5-sulfamoyl-2-thenylaminophenyl)-tetrazole is prepared from a lyophilizate of the mixture shortly before the injection, by dissolving the dry mixture in an appropriate aqueous solvent. However, this preparation of an injection solution suffers from certain disadvantage. Thus, the preparation of the lyophilizate requires laborious and expensive techniques. The lyophilizate must be sterilized by laborious sterile filtration and a portion of non-sterile, pyrogen-containing batches cannot be avoided. Furthermore, an additional expenditure of time is needed for dissolving the lyophilizate before administration.

This complicated process was necesitated after it was determined that normal aqueous potassium canrenoate solutions cannot be used for injections because they are not sufficiently stable. As is known, canrenoic acid itself is very sparingly water-soluble so that, in place thereof, it is necessary to employ the sufficiently water-soluble potassium salt of canrenoic acid for the preparation of aqueous injection solutions. The equivalence point of potassium canrenoate lies at pH 10.2. However, after a conventional heat sterilization at 120° C, unexplicable turbidities arise, which make these solutions unsuitable for intravenous injection.

There has been a need for solution-stable, injection-compatible canrenoate preparations.

Therefore, the present invention provides canrenoate preparations which are stable in the form of solutions and physiologically compatible in injectable form and can be sterilized at 120° C.

The preparations of the invention are injectable alkaline solutions ready for injection, comprising an alkali metal canrenoate or a mixture of an alkali metal canrenoate and a diuretic, water and a physiologically compatible alkaline buffer, wherein the buffer has a low buffer capacity and give a pH range of 10.2 to 11.2.

The present invention also provides a process for the production of these injectable solutions ready for injection, wherein canrenoic acid or a mixture thereof with at least one other diuretic is suspended in an aqueous solution of a physiologically compatible buffer which, in the amount used, has a low buffer capacity and buffers in the pH range of 10.2 to 11.2, whereafter the suspension is adjusted with an aqueous solution of an alkali to a pH value of 10.6 to 11.0.

Solutions thus prepared can be readily sterilizable by heating to 120° C for 20 minutes. We have also found that they can be stored for at least 3 years without turbidities being formed and without a chemical change of the active materials occurring. These solutions are compatible with the veins, i.e., they can be administered intravenously in undiluted form.

Because of their low buffer capacity, they do not give rise to significant pH value changes at the point of injection so that an undiluted administration thereof is possible. Buffer capacities are preferred which are not more than 0.1 equivalents per liter of injection solution, i.e., a normal ampoule content of 10 ml. of injection solution should be able to be brought to the pH value of the blood of 7.4 by the addition of, at most, 10 ml. 0.1N hydrochloric acid.

The buffer employed in the injectable solution according to the present invention can be, for example, a sodium or potassium carbonate buffer, a sodium or potassium phosphate buffer or a glycinate buffer, for example a potassium glycinate buffer, as well as a similar buffer mixture based on amino acids which ensures an optimum stabilization of the solution during heat sterilization thereof.

The active material in the injection solution according to the present invention can be not only an alkali metal canrenoate, but also a mixture thereof with at least one other diuretic. However, a potassium canrenoate injection solution is preferred, as well as an injection solution containing a mixture of potassium canrenoate and 5-(4-chloro-5-sulfamoyl-2-thenylaminophenyl)-tetrazole or a mixture of potassium canrenoate and furosemide.

About 50 to 250 mg. active material are preferably employed per ampoule.

The alkali metal canrenoate, preferably potassium canrenoate, and the 5-(4-chloro-5-sulfamoyl-2-thenylaminophenyl)-tetrazole or furosemide can be used in a weight ratio of 50:1 to 4:1 and preferably of 40:1 to 10:1.

The injections solution according to the present invention can also be mixed with a 5% glucose infusion solution or an isotonic solution of sodium chloride and thereafter administered by infusion.

The following examples are given for the purpose of illustrating the present invention:

EXAMPLE 1

10 ml Injection Solution Of Potassium Canrenoate Ready For Injection 100 g tripotassium phosphate were dissolved in about 80 liters of water suitable for injection purposes and thereafter 1.806 kg of canrenoic acid were suspended therein portionwise. The pH was adjusted to 11.0 with a 5% aqueous potassium hydroxide solution and the solution was made up to 100 liters with water suitable for injection purposes.

The solution obtained was filtered through 20 layers of EKS II 20 × 20 cm. The first 15 liters of the filtrate were pre-runnings and were returned to the batch. The membrane filtration took place directly on a filling machine through Millipore GS or Sartorius SM 11307 filters. Subsequently, the filtered solution was filled into 10 ml ampoules which were then sterilized at 120° C for 20 minutes.

A clear injection solution was thus obtained which was ready for injection but which could be stored for at least 3 years without decomposition or turbidity. The pH of this injection solution was 10.9. The buffer capacity corresponds to 5.7 ml of 0.1N hydrochloric acid, which were needed per ampoule for decreasing the pH value from 10.9 to 7.4.

EXAMPLE 2

20 ml Injection Solution Of Potassium Canrenoate Ready For Injection 100 g tripotassium phosphate were dissolved in about 100 liters of water suitable for injection purposes and 1.806 kg canrenoic acid were suspended therein portionwise. The pH was adjusted to 11.0 with a 5% aqueous potassium hydroxide solution and the solution was made up to 200 liters with water suitable for injection purposes. All the further steps were carried out analogously to Example 1 but with filling into 20 ml ampoules.

A clear injection solution was thus obtained which was ready for injection but which could be stored for at least 3 years without decomposition and turbidity. The pH value of this injection solution was 10.8. The buffer capacity corresponds to 5.5 ml of 0.1N hydrochloric acid, which were needed per ampoule for decreasing the pH value from 10.8 to 7.4.

EXAMPLE 3

10 ml Injection Solution Of Potassium Canrenoate Ready For Injection 200 g glycine were dissovled in about 80 liters of water suitable for injection purposes and thereafter 1.806 kg canrenoic acid were suspended therein portionwise. The pH was adjusted to 11.0 with a 5% aqueous potassium hydroxide solution and the solution was made up to 100 liters with water suitable for injection purposes. All the further steps were carried out analogously to Example 1.

A clear injection solution was thus obtained which was ready for injection but which could be stored for at least 3 years without decomposition or turbidity. The pH value of this injection solution was 10.6. The buffer capacity corresponds to 7.0 ml of 0.1N hydrochloric acid, which were needed per ampoule for decreasing the pH value from 10.6 to 7.4.

EXAMPLE 4

20 ml Injection Solution Of Potassium Canrenoate Ready For Injection 200 g glycine were dissolved in about 100 liters of water suitable for injection purposes and 1.806 kg canrenoic acid were suspended therein portionwise. The pH was adjusted to 11.0 with a 5% aqueous potassium hydroxide solution and the solution was made up to 200 liters with water suitable for injection purposes. All further steps were carried out analogously to Example 1 but with filling into 20 ml ampoules.

A clear injection solution was thus obtained which was ready for injection but which could be stored for at least 3 years without decomposition and turbidity. The pH value of this injection solution was 10.6. The buffer capacity corresponds to 7.25 ml of 0.1N hydrochloric acid, which were needed per ampoule for decreasing the pH value from 10.6 to 7.4.

EXAMPLE 5

10 ml Injection Solution Of Potassium Canrenoate and 5-(4-chloro-5-sulfamoyl-2-thenylaminophenyl)-tetrazole Ready For Injection 100 g tripotassium phosphate were dissolved in about 80 liters of water suitable for injection purposes. Thereafter, a mixture of 1.806 kg canrenoic acid and 50 g 5-(4-chloro-5-sulfamoyl-2-thenylaminophenyl)-tetrazole was suspended therein portionwise. The pH was adjusted to 11.0 with a 5% aqueous potassium hydroxide solution and the solution was made up to 100 liters with water suitable for injection purposes. All the further steps were carried out analogously to Example 1.

A clear injection solution was thus obtained which was ready for injection but which could be stored for at least 3 years without decomposition and turbidity. The pH value of this injection solution was 10.9. The buffer capacity corresponds to 5.8 ml of 0.1N hydrochloric acid, which were needed per ampoule for decreasing the pH value from 10.9 to 7.4.

EXAMPLE 6

20 ml Injection Solution Of Potassium Canrenoate and 5-(4-chloro-5-sulfamoyl-2-thenylaminophenyl)-tetrazole Ready For Injection 100 g tripotassium phospate were dissolved in about 100 liters of water suitable for injection purposes and 1.806 kg canrenoic acid, as well as 100 g 5-(4-chloro-5-sulfamoyl-2-thenylaminophenyl)-tetrazole, were suspended therein. The pH was adjusted to 11.0 with a 5% aqueous potassium hydroxide solution and the solution was made up to 200 liters with water suitable for injection purposes. All the further steps were carried out analogously to Example 1 but with filling into 20 ml ampoules.

A clear injection solution was thus obtained which was ready for injection but which could be stored for at least 3 years without decomposition and turbidity. The pH value of this solution was 10.8. The buffer capacity corresponds to 5.7 ml of 0.1N hydrochloric acid, which were needed per ampoule for decreasing the pH value from 10.8 to 7.4.

EXAMPLE 7

10 ml Injection Solution Of Potassium Canrenoate and Furosemide Ready For Injection 100 g tripotassium phosphate were dissolved in about 80 liters of water suitable for injection purposes. Thereafter, a mixture of 1.806 kg canrenoic acid and 20 g furosemide were suspended therein portionwise. The pH was adjusted to 11.0 with a 5% aqueous potassium hydroxide solution and the solution was made up to 100 liters with water suitable for injection purposes. All the further steps were carried out analogously to Example 1.

A clear injection solution was thus obtained which was ready for injection but which could be stored for at least 3 years without decomposition and turbidity. The pH value of this injection solution was 10.9. The buffer capacity corresponds to 5.8 ml of 0.1N hydrochloric acid, which were needed for decreasing the pH value from 10.9 to 7.4.

EXAMPLE 8

10 ml Injection Solution Of Potassium Canrenoate Ready For Injection 200 g potassium carbonate were dissolved in about 80 liters of water suitable for injection purposes and 1.806 kg canrenoic acid were then suspended therein portionwise. The pH value was then adjusted to 11.0 by the addition of a 5% aqueous solution of potassium hydroxide and the solution was made up to 100 liters with water suitable for injection purposes. All the further steps were carried out analogously to Example 1.

There was thus obtained a clear injection solution which was ready for injection but which could be stored for at least 3 years without decomposition or turbidity. The pH of this injection solution was 10.7. The buffer capacity corresponds to 6.0 ml of 0.1N hydrochloric acid, which were needed per ampoule for decreasing the pH value from 10.6 to 7.4.

EXAMPLE 9

20 ml Injection Solution Of Potassium Canrenoate Ready For Injection 200 g potassium carbonate were dissolved in about 100 liters of water suitable for injection purposes and 1.806 kg canrenoic acid suspended therein portionwise. The solution was adjusted to pH 11.0 with a 5% aqueous potassium hydroxide solution. The solution was then made up to 200 liters with water suitable for injection purposes. All further steps were carried out analogously to Example 1 except that 20 ml ampoules were filled with the solution.

There was thus obtained a clear injection solution which was ready for injection but which could be stored for at least 3 years without decomposition or turbidity. The pH of this solution was 10.7. The buffer capacity corresponds to 6.2 ml of 0.1N hydrochloric acid, which were needed per ampoule for decreasing the pH value from 10.7 to 7.4.

It will be understood that the specification and examples are illustrative but not limitative of the present invention and that other embodiments within the spirit and scope of the invention will suggest themselves to those skilled in the art.

What is claimed is:

1. An injectable alkaline solution comprising
   (a) as active ingredient, at least one alkali metal canrenoate or a mixture of an alkali metal canrenoate and an additional diuretic, and
   (b) water and a physiologically compatible alkaline buffer, wherein the buffer has a low buffer capacity and gives a pH range of 10.2 to 11.2, and is selected from sodium or potassium phosphate, sodium or potassium carbonate, and sodium or potassium glycinate.

2. A solution as claimed in claim 1 wherein said alkaline buffer is tripotassium phosphate.

3. A solution as claimed in claim 1 wherein said alkaline buffer is potassium carbonate.

4. A solution as claimed in claim 1 wherein said alkaline buffer is potassium glycinate.

5. A solution as claimed in claim 1 wherein the buffer capacity of said alkaline buffer is not more than 0.1 equivalent per liter of injectable solution.

6. A solution as claimed in claim 1 comprising as active ingredients a mixture of an alkali metal canrenoate and an additional diuretic.

7. A solution as claimed in claim 6 wherein said additional diuretic is 5-(4-chloro-5-sulfamoyl-2-thenylaminophenyl)-tetrazole.

8. A solution as claimed in claim 6 wherein said additional diuretic is 4-chloro-N-(2-furylmethyl)-5-sulfamoylanthranilic acid.

9. A solution as claimed in claim 6 wherein the weight ratio of said alkali metal canrenoate to said additional diuretic is from 50:1 to 4:1.

10. A solution as claimed in claim 9 wherein the weight ratio of said alkali metal canrenoate to said additional diuretic is from 40:1 to 10:1.

11. A process for the production of an injectable solution ready for injection as claimed in claim 1 wherein canrenoic acid or a mixture thereof with at least one other diuretic is suspended in an aqueous solution of a physiologically compatible buffer which, in the amount used, has a low buffer capacity and buffers in the pH range of 10.2 to 11.2, whereafter the suspension is adjusted with an aqueous solution of an alkali to a pH of 10.6 to 11.0.

12. A process as claimed in claim 7 wherein the solution is sterilized by heating to 120° C for 20 minutes.

* * * * *